(12) United States Patent
Yamaki (10) Patent No.: US 12,102,297 B2
(45) Date of Patent: Oct. 1, 2024

(54) ENDOSCOPE SYSTEM AND OPERATION METHOD THEREFOR

(71) Applicant: FUJIFILM Corporation, Tokyo (JP)

(72) Inventor: Teppei Yamaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 176 days.

(21) Appl. No.: 18/045,054

(22) Filed: Oct. 7, 2022

(65) Prior Publication Data

US 2023/0113987 A1    Apr. 13, 2023

(30) Foreign Application Priority Data

Oct. 11, 2021  (JP) .................................. 2021-166739

(51) Int. Cl.
| | | |
|---|---|---|
| *A61B 1/045* | (2006.01) | |
| *A61B 1/00* | (2006.01) | |
| *A61B 1/005* | (2006.01) | |
| *A61B 1/04* | (2006.01) | |
| *A61B 1/06* | (2006.01) | |
| *A61B 5/1455* | (2006.01) | |

(52) U.S. Cl.
CPC ............ *A61B 1/045* (2013.01); *A61B 1/0638* (2013.01)

(58) Field of Classification Search
CPC ... A61B 1/045; A61B 1/0638; A61B 1/00006; A61B 1/0655
See application file for complete search history.

(56) References Cited

U.S. PATENT DOCUMENTS

| | | | |
|---|---|---|---|
| 2013/0245410 A1* | 9/2013 | Saito ..................... | A61B 1/0051 600/339 |
| 2017/0366724 A1* | 12/2017 | Murakita ........... | A61B 1/00009 |
| 2020/0163538 A1* | 5/2020 | Takahashi .............. | A61B 1/043 |
| 2020/0174245 A1* | 6/2020 | Nishihara ............ | A61B 1/0002 |

FOREIGN PATENT DOCUMENTS

JP    2013-188365 A    9/2013

* cited by examiner

*Primary Examiner* — Alazar Tilahun
(74) *Attorney, Agent, or Firm* — Studebaker & Brackett PC (57) ABSTRACT

A sensor gain applied to a first illumination light image and a second illumination light image is set on the basis of a target light amount of first illumination light. A second target brightness is calculated on the basis of the second illumination light image in which the sensor gain is reflected, and a target light amount of the second illumination light is calculated on the basis of the second target brightness. A second digital gain that is applied to the second illumination light image and varies depending on the second target brightness and the sensor gain is set.

10 Claims, 9 Drawing Sheets

| TARGET LIGHT AMOUNT OF FIRST ILLUMINATION LIGHT | EXPOSURE CONTROL FOR FIRST ILLUMINATION LIGHT IMAGE |
|---|---|
| LESS THAN FIRST SPECIFIED VALUE | LIGHT AMOUNT CONTROL FOR FIRST ILLUMINATION LIGHT SENSOR GAIN = 1 |
| FIRST SPECIFIED VALUE OR MORE | SENSOR GAIN > 1 |

FIG. 8

| TARGET LIGHT AMOUNT OF FIRST ILLUMINATION LIGHT | EXPOSURE CONTROL FOR FIRST ILLUMINATION LIGHT IMAGE | TARGET LIGHT AMOUNT OF SECOND ILLUMINATION LIGHT | EXPOSURE CONTROL FOR SECOND ILLUMINATION LIGHT IMAGE |
|---|---|---|---|
| LESS THAN FIRST SPECIFIED VALUE | LIGHT AMOUNT CONTROL FOR FIRST ILLUMINATION LIGHT  SENSOR GAIN = 1 | LESS THAN SECOND SPECIFIED VALUE | LIGHT AMOUNT CONTROL FOR SECOND ILLUMINATION LIGHT DIGITAL GAIN = 1 |
| | | SECOND SPECIFIED VALUE OR MORE | DIGITAL GAIN > 1 |
| FIRST SPECIFIED VALUE OR MORE | SENSOR GAIN > 1 | LESS THAN SECOND SPECIFIED VALUE | LIGHT AMOUNT CONTROL FOR SECOND ILLUMINATION LIGHT DIGITAL GAIN = 1 |
| | | SECOND SPECIFIED VALUE OR MORE | DIGITAL GAIN > 1 |

ENDOSCOPE SYSTEM AND OPERATION METHOD THEREFOR

CROSS-REFERENCE TO RELATED APPLICATIONS

This application claims priority under 35 U.S.C § 119(a) to Japanese Patent Application No. 2021-166739 filed on 11 Oct. 2021. The above application is hereby expressly incorporated by reference, in its entirety, into the present application.

BACKGROUND OF THE INVENTION

1. Field of the Invention

The present invention relates to an endoscope system that acquires and displays a plurality of types of images obtained by emitting light while switching a plurality of pieces of illumination light, and an operation method therefor.

2. Description of the Related Art

In an endoscope system, an image of an observation target is obtained by illuminating the observation target with illumination light and picking up an image of the observation target. In recent years, as disclosed in JP2013-188365A (corresponding to US2013/245410A1), in a case of acquiring and displaying a plurality of types of images obtained by emitting light while switching a plurality of pieces of illumination light, an exposure amount in a frame based on each piece of illumination light is set on the basis of brightness information of a key moving image and a light amount ratio of the plurality of pieces of illumination light.

SUMMARY OF THE INVENTION

Control of an exposure amount during endoscopy includes control of a sensor gain of an image pick-up sensor used for picking up an image of an observation target, in addition to control of a light amount of illumination light. In a case where a plurality of pieces of illumination light are switched and emitted, it is preferable to switch sensor gains in accordance with switching of the pieces of illumination light. However, since the sensor gain switching is generally performed by transmitting a gain switching command from a processor device to an image pick-up sensor of an endoscope, there may be a deviation between an illumination light switching timing and a sensor gain switching timing.

For example, in a case where switching from first illumination light to second illumination light is performed, a switching timing of the sensor gain is delayed from a switching timing of the illumination light, and thus a sensor gain for a first illumination light image set for the first illumination light image based on the first illumination light may be reflected in a second illumination light image based on the second illumination light. In this case, the brightness of the second illumination light image may not be able to be matched with a target brightness.

An object of the present invention is to provide an endoscope system and an operation method therefor capable of adjusting each image to a target brightness even in a case where a sensor gain is used to control an exposure amount of each image in a case of acquiring and displaying a plurality of types of images corresponding to respective pieces of illumination light by emitting light while switching a plurality of pieces of illumination light.

According to the present invention, there is provided an endoscope system including a light source unit that automatically switches and emits first illumination light and second illumination light having different emission spectra according to a specific light emission pattern; and a processor, in which the processor acquires a first illumination light image based on the first illumination light and a second illumination light image based on the second illumination light, calculates a target light amount of the first illumination light on the basis of a first target brightness of the first illumination light image, sets a sensor gain applied to the first illumination light image and the second illumination light image on the basis of the target light amount of the first illumination light, calculates a second target brightness on the basis of the second illumination light image in which the sensor gain is reflected, and calculates a target light amount of the second illumination light on the basis of the second target brightness, and sets a second digital gain that is applied to the second illumination light image and varies depending on the second target brightness and the sensor gain.

It is preferable that, in a case where the target light amount of the second illumination light is equal to or more than a second specified value, the processor sets the second digital gain such that the second target brightness is obtained, and a sum of the sensor gain and the second digital gain is less than an addition upper limit value. It is preferable that, in a case where the target light amount of the first illumination light is less than a first specified value, the processor sets the fixed sensor gain, and sets the second digital gain according to the second target brightness within a range of the addition upper limit value. It is preferable that, in a case where the target light amount of the first illumination light is equal to or more than a first specified value, the processor sets the sensor gain to vary according to the target light amount of the first illumination light, and sets the second digital gain such that the second digital gain is reduced as the sensor gain is increased within a range of the addition upper limit value.

It is preferable that, in a case where the sensor gain exceeds a sensor gain upper limit value, the processor performs a process of clipping the sensor gain to the sensor gain upper limit value. It is preferable that, in a case where the sum of the sensor gain and the second digital gain exceeds the addition upper limit value, the processor performs clip processing for aligning the second digital gain with a value obtained by subtracting the sensor gain from the addition upper limit value. It is preferable that the second target brightness is reduced as the sensor gain is increased.

It is preferable that the processor sets a fixed first digital gain that is a first digital gain applied to the first illumination light image and does not change regardless of the sensor gain, in addition to the setting of the second digital gain.

It is preferable that, in a case where the first illumination light for a plurality of frames is continuously emitted and then the second illumination light for at least one frame is emitted in the specific light emission pattern, and the second digital gain greater than 1 is set, the set second digital gain is reflected in the second illumination light image acquired after the first illumination light is continuously emitted.

According to the present invention, there is provided an operation method for an endoscope system including a light source unit that automatically switches and emits first illumination light and second illumination light having different emission spectra according to a specific light emission pattern and a processor, the operation method of causing the processor to execute a step of acquiring a first illumination light image based on the first illumination light and a second illumination light image based on the second illumination light; a step of calculating a target light amount of the first illumination light on the basis of a first target brightness of the first illumination light image; a step of setting a sensor gain applied to the first illumination light image and the second illumination light image on the basis of the target light amount of the first illumination light; a step of calculating a second target brightness on the basis of the second illumination light image in which the sensor gain is reflected, and calculates a target light amount of the second illumination light on the basis of the second target brightness; and a step of setting a second digital gain that is applied to the second illumination light image and varies depending on the second target brightness and the sensor gain.

According to the present invention, it is possible to adjust each image to a target brightness even in a case where a sensor gain is used to control an exposure amount of each image in a case of acquiring and displaying a plurality of types of images corresponding to respective pieces of illumination light by emitting light while switching a plurality of pieces of illumination light.

DESCRIPTION OF THE PREFERRED EMBODIMENTS

Figure 1:
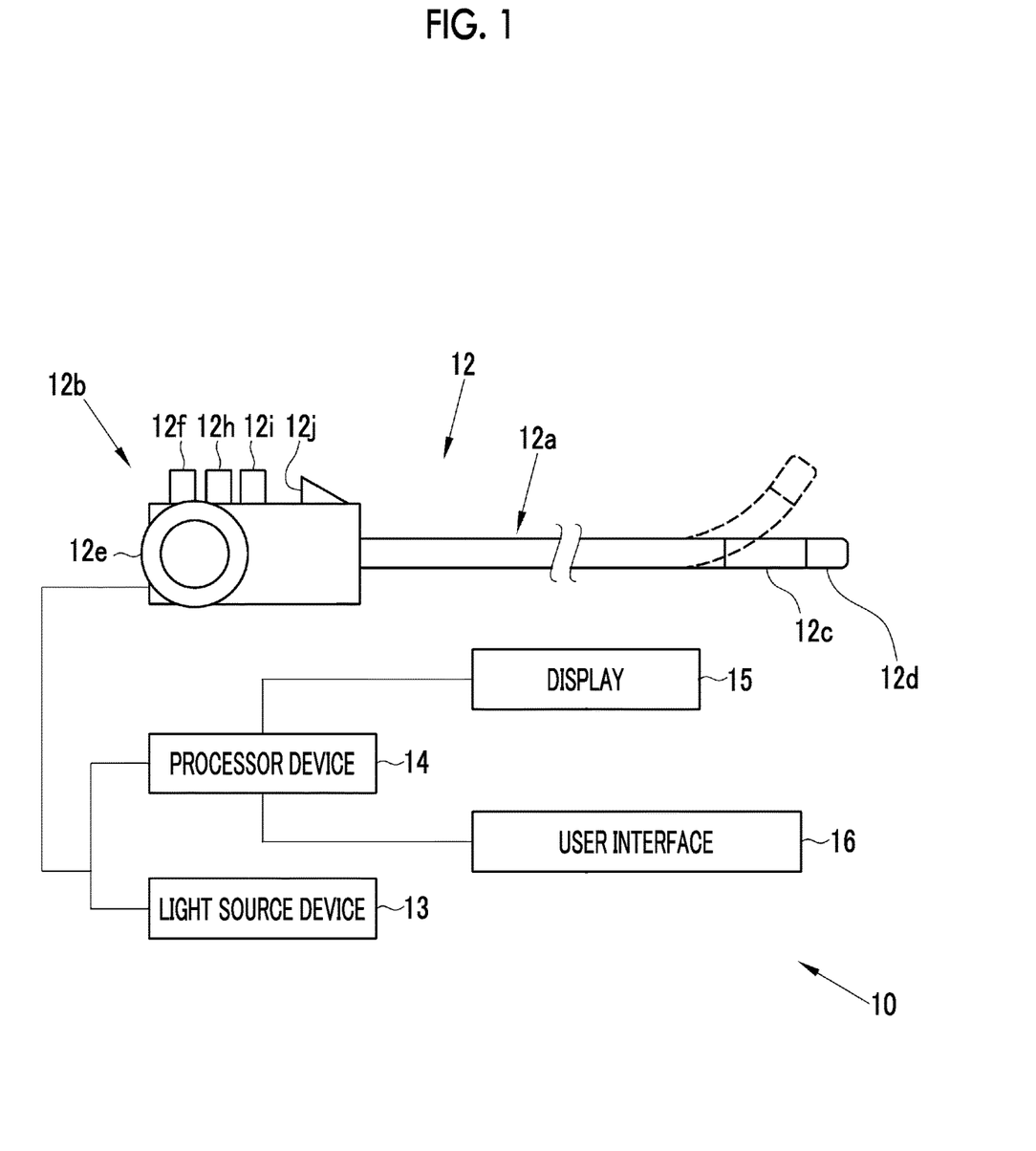
FIG. 1 is a schematic diagram of an endoscope system.

As shown in FIG. 1, an endoscope system 10 includes an endoscope 12, a light source device 13, a processor device 14, a display 15, and a user interface 16. The endoscope 12 is optically or electrically connected to the light source device 13 and electrically connected to the processor device 14.

The endoscope 12 has an insertion part 12a, an operating part 12b, a bendable part 12c, and a tip part 12d. The insertion part 12a is inserted into the body of a subject. The operating part 12b is provided at a base end portion of the insertion part 12a. The bendable part 12c and the tip part 12d are provided on a tip end side of the insertion part 12a. The bendable part 12c is bent by operating an angle knob 12e of the operating part 12b. The tip part 12d is directed in a desired direction in a case where the bendable part 12c is bent. A forceps channel (not shown) for inserting a treatment tool or the like is provided from the insertion part 12a to the tip part 12d. The treatment tool is inserted into the forceps channel from a forceps port 12j.

Inside the endoscope 12, an optical system for forming a subject image and an optical system for irradiating a subject with illumination light are provided. The operating part 12b is provided with an angle knob 12e, an observation mode selector switch 12f, a still image acquisition instruction switch 12h, and a zoom operating part 12i. The observation mode selector switch 12f is used for an observation mode switching operation. The still image acquisition instruction switch 12h is used for an instruction for acquiring a still image of a subject. The zoom operating part 12i is used for an operation of enlarging or reducing an observation target.

The light source device 13 generates illumination light. The processor device 14 performs system control on the endoscope system 10 and further performs image processing or the like on an image signal transmitted from the endoscope 12 to generate an endoscopic image or the like. The display 15 displays an endoscopic image transmitted from the processor device 14. The user interface 16 includes a keyboard, a mouse, a microphone, a tablet terminal, a touch pen, a foot switch, or the like, and receives input operations such as function settings.

Figure 2:
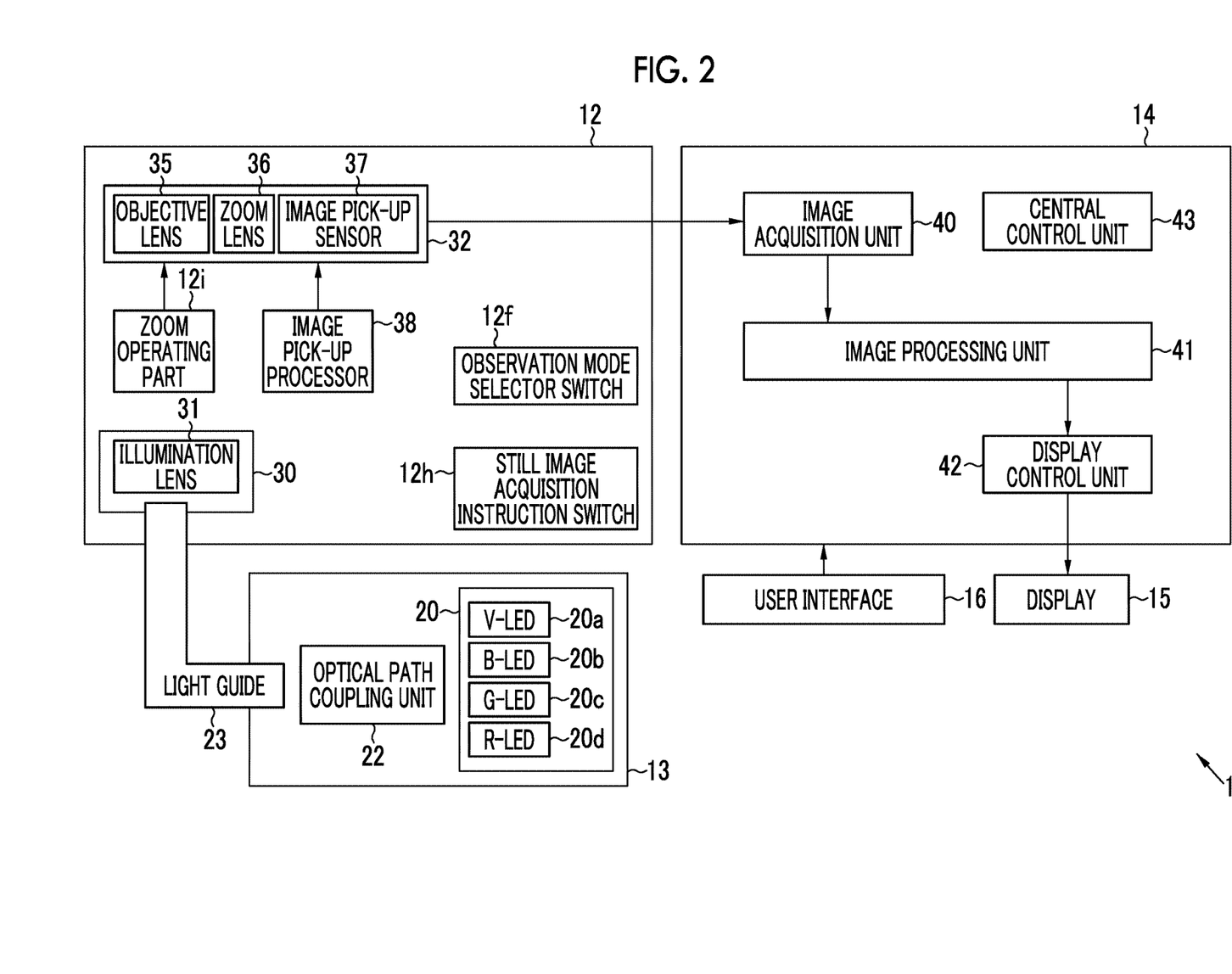
FIG. 2 is a block diagram showing a function of the endoscope system.

As shown in FIG. 2, the light source device 13 includes a light source unit 20 and an optical path coupling unit 22. The light source unit 20 has a plurality of semiconductor light sources, and turns on or off each thereof. In a case where a plurality of semiconductor light sources are turned on, illumination light that illuminates a subject is emitted by controlling an amount of light emitted from each semiconductor light source. The light source unit 20 includes four color LEDs such as a violet light emitting diode (V-LED) 20a, a blue light emitting diode (B-LED) 20b, a green light emitting diode (G-LED) 20c, and a red light emitting diode (R-LED) 20d. The light source unit 20 may be built in the endoscope 12.

Optical paths of pieces of light emitted by the respective LEDs 20a to 20d are coupled by the optical path coupling unit 22 configured with a mirror, a lens, and the like. The light of which the optical paths are coupled by the optical path coupling unit 22 is incident to a light guide 23. The light guide 23 propagates the light from the optical path coupling unit 22 to the tip part 12d of the endoscope 12.

An illumination optical system 30 and an image pick-up optical system 32 are provided at the tip part 12d of the endoscope 12. The illumination optical system 30 has an illumination lens 31, and the illumination light propagated by the light guide 23 is applied to a subject via the illumination lens 31. On the other hand, in a case where the light source unit 20 is built in the tip part 12d of the endoscope 12, light is emitted toward a subject via the illumination lens of the illumination optical system without using the light guide.

The image pick-up optical system 32 includes an objective lens 35, a zoom lens 36, and an image pick-up sensor 37. Light from a subject due to irradiation with the illumination light is incident to the image pick-up sensor 37 via the objective lens 35 and the zoom lens 36. Consequently, an image of the subject is formed on the image pick-up sensor 37. The zoom lens 36 is a lens for enlarging the subject and is moved between the telephoto end and the wide end by operating the zoom operating part 12i.

The image pick-up sensor 37 is preferably a charge-coupled device (CCD) or a complementary metal oxide semiconductor (CMOS). An image pick-up processor 38 controls the image pick-up sensor 37. Specifically, an image signal is output from the image pick-up sensor 37 by the image pick-up processor 38 reading a signal of the image pick-up sensor 37. The output image signal is transmitted to the processor device 14.

The processor device 14 includes an image acquisition unit 40, an image processing unit 41, a display control unit 42, and a central control unit 43. In the processor device 14, the central control unit 43 configured with a processor operates a program in a program memory (not shown) to realize the functions of the image acquisition unit 40, the image processing unit 41, and the display control unit 42.

The image acquisition unit 40 acquires an image signal from the endoscope 12 as an image signal for an endoscopic image. The image processing unit 41 performs various types of signal processing such as a defect correction process, an offset process, a demosaic process, a matrix process, white balance adjustment, a gamma conversion process, and a YC conversion process on the image signal acquired by the image acquisition unit 40. Next, image processing including a 3×3 matrix process, a gradation transformation process, a color conversion process such as three-dimensional look up table (LUT) processing, a color emphasis process, and a structure emphasis process such as spatial frequency emphasis is performed to generate a color endoscopic image. The display control unit 42 displays various types of information including the endoscopic image generated by the image processing unit 41 on the display 15.

The endoscope system 10 includes a mono-light emission mode and a multi-light emission mode as light emission modes for emitting illumination light. By operating the observation mode selector switch 12f, the light emission modes can be switched via the central control unit 43. The mono-light emission mode is a mode in which the light source unit 20 continuously applies illumination light having the same spectrum to illuminate a subject that is an observation target. The multi-light emission mode is a mode in which a plurality of pieces of illumination light having different spectra are applied while being automatically switched therebetween according to a specific light emission pattern to illuminate a subject.

The illumination light includes first illumination light L1 and second illumination light L2 having a spectrum different from that of the first illumination light. The first illumination light L1 is preferably used for screening observation by giving brightness to the entire subject. The second illumination light L2 is preferably used to emphasize a specific structure such as a duct or a blood vessel of a mucous membrane that is a subject. In the mono-light emission mode, either the first illumination light or the second illumination light is emitted. In the multi-light emission mode, the first illumination light and the second illumination light are switched and emitted according to a specific light emission pattern.

The first illumination light L1 is preferably light having a wide band such as white light. The second illumination light L2 is preferably includes, for example, second illumination light L2SP for emphasizing a superficial blood vessel, second illumination light L2SQ for emphasizing a polar superficial blood vessel shallower than a superficial blood vessel, second illumination light L2SR for generating an oxygen saturation image using a difference in a light absorption coefficient of an oxidized hemoglobin and a reduced hemoglobin, and second illumination light L2SS for generating a color difference expanded image in which a color difference between a plurality of subject ranges is expanded. These four types of second illumination light L2SP, L2SQ, L2SR, and L2SS have different spectra.

In the light source device 13, light amounts of the violet light V, the blue light B, the green light G, and the red light R of four colors are independently controlled, the light amounts are changed, and the first illumination light L1 or the second illumination light L2 (for example, the second Illumination light L2SP, the second illumination light L2SQ, the second illumination light L2SR, and the second illumination light L2SS) are emitted. Light emission control in the mono-light emission mode and the multi-light emission mode in the light source device 13 is performed by a light source processor (not shown).

In the case of the mono-light emission mode, illumination light having the same spectrum is continuously emitted for each frame. For example, a first illumination light image is displayed on the display 15 by illuminating a subject with the first illumination light for each frame and picking up an image of the subject. A second illumination light image is displayed on the display 15 by illuminating the subject with the second illumination light for each frame and picking up an image of the subject. The frame is a unit of a period including at least a period from the timing of light emission to the completion of reading an image signal in the image pick-up sensor 37.

In the case of the multi-light emission mode, each of the LEDs 20a to 20d is controlled to automatically switch between the first illumination light and the second illumination light according to a specific light emission pattern and to emit light. Specifically, control is performed such that amounts of the violet light V, the blue light B, the green light G, and the red light R are changed for each specific frame F according to a specific light emission pattern.

Figure 3:
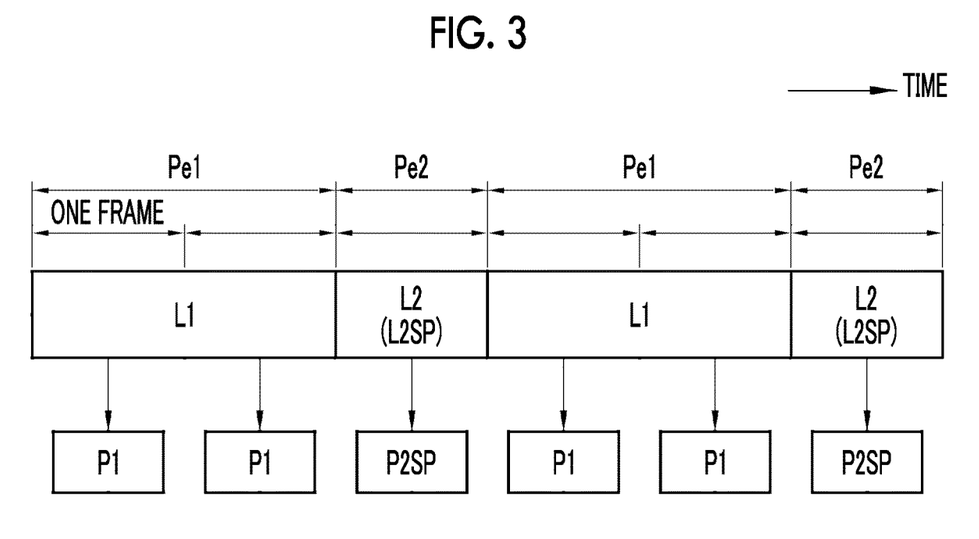
FIG. 3 is an explanatory diagram showing a first light emission pattern.

An example of the light emission pattern will be described below. For example, in a first light emission pattern, as shown in FIG. 3, a pattern is repeated in which the first illumination light L1 for two frames is emitted in a first light emission period Pe1 for illuminating the subject with the first illumination light L1, and the second illumination light L2 for one frame is emitted in a second light emission period Pe2 for illuminating the subject with the second illumination light L2. In the first light emission pattern, the same second illumination light L2SP is emitted in each second light emission period Pe2.

In the figure, the arrow indicates a direction in which time advances. In the first light emission pattern, a first illumination light image P1 for two frames is obtained in the first light emission period Pe1, and a second illumination light image P2SP for one frame is obtained in the second light emission period Pe2. In the first light emission pattern, the first illumination light L1 having a different spectrum may be emitted in each first light emission period Pe1 (the same applies to a second light emission pattern and a third light emission pattern that will be described below).

Figure 4:
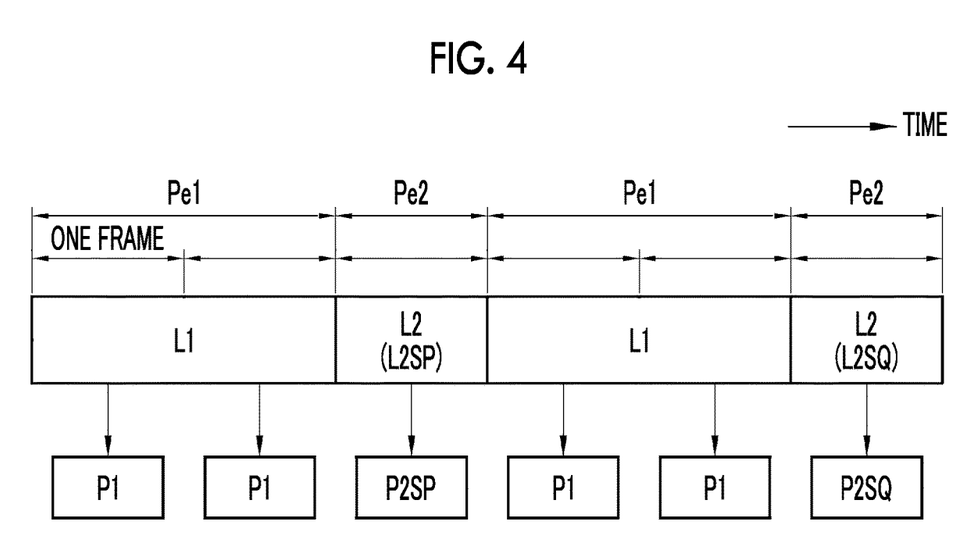
FIG. 4 is an explanatory diagram showing a second light emission pattern.

In the second light emission pattern, as shown in FIG. 4, a pattern is repeated in which the first illumination light L1 for two frames is emitted in the first light emission period Pe1 and the second illumination light L2 for one frame is emitted in the second light emission period Pe2. In this case, in each second light emission period Pe2, the second illumination light L2 having a different spectrum is emitted. Specifically, in the second light emission period Pe2, the second illumination light L2SP and the second illumination light L2SQ are alternately emitted. In the second light emission pattern, the first illumination light image P1 for two frames is obtained in the first light emission period Pe1, and the second illumination light image P2SP and a second illumination light image P2SQ are obtained in the respective second light emission periods Pe2.

Figure 5:
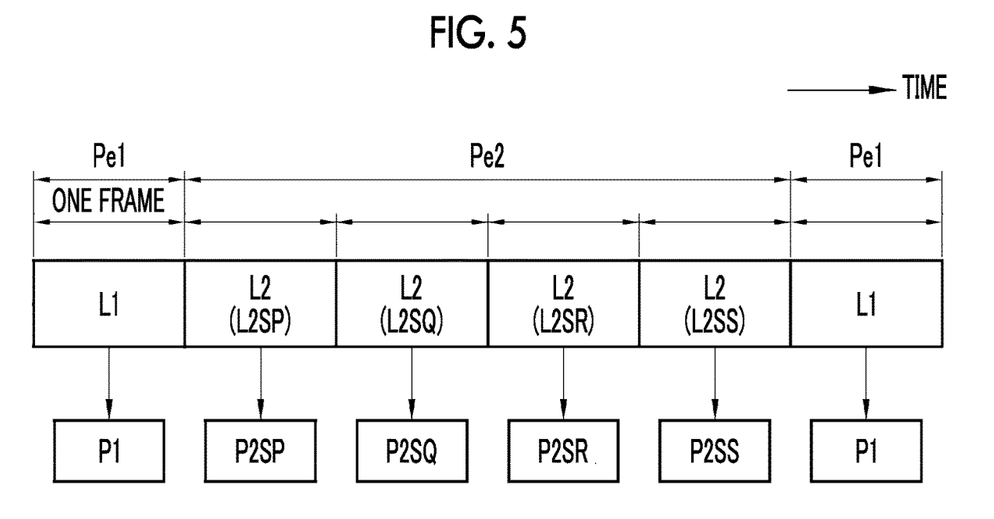
FIG. 5 is an explanatory diagram showing a third light emission pattern.

In the third light emission pattern, as shown in FIG. 5, a pattern is repeated in which the first illumination light L1 for one frame is emitted in the first light emission period Pe1 and the second illumination light L2 for four frames is emitted in the second light emission period Pe2. In this case, in the second light emission period Pe2, as the second illumination light L2, the second illumination light L2SP, the second illumination light L2SQ, the second illumination light L2SR, and the second illumination light L2SS having different spectra are automatically switched and emitted for each frame. In the third light emission pattern, the first illumination light image P1 is obtained in the first light emission period Pe1, and the second illumination light images P2SP, P2SQ, P2SR, and P2SS are obtained in the second light emission period Pe2. In the third light emission pattern, four types of second illumination light L2 having different spectra are switched and emitted, but a plurality of types of second illumination light other than the four types may be switched and emitted.

Details of exposure control for the first illumination light image and the second illumination light image in the multi-light emission mode will be described below. The exposure control for the first illumination light image includes control of the light amount LM1 of the first illumination light L1, processing of a sensor gain for the first illumination light image, and processing of a first digital gain for the first illumination light image. The exposure control for the second illumination light image includes control of the light amount LM2 of the second illumination light L2, processing of a sensor gain for the second illumination light image, and processing of a second digital gain for the second illumination light image.

Figure 6:
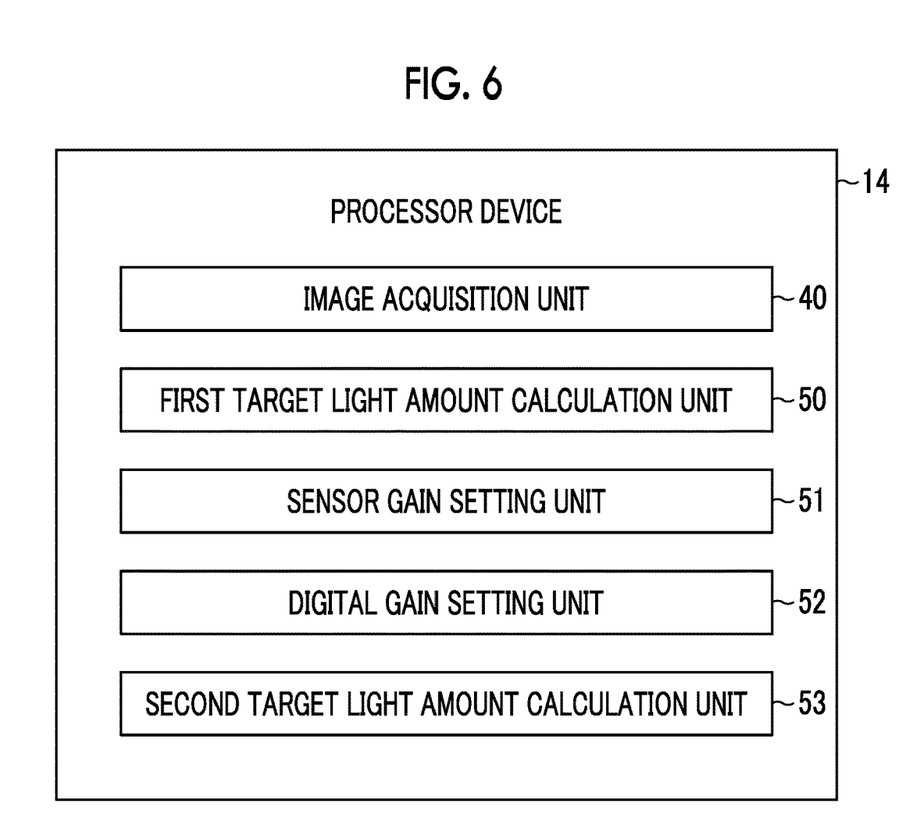
FIG. 6 is a block diagram showing functions of a processor device.

In order to process the exposure control for the first illumination light image and the second illumination light image, as shown in FIG. 6, the processor device 14 includes a first target light amount calculation unit 50, a sensor gain setting unit 51, a digital gain setting unit 52, and a second target light amount calculation unit 53 in addition to the image acquisition unit 40. In the present embodiment, it is assumed that the same sensor gain is applied to the first illumination light image and the second illumination light image, and a second target brightness is calculated on the basis of the second illumination light image to which the sensor gain is applied, a target light amount of the second illumination light is calculated on the basis of the second target brightness, and a second digital gain that varies depending on the second target brightness and the sensor gain is set.

Consequently, even though there is a deviation between a switching timing of the illumination light and a switching timing of the sensor gain, the second target brightness calculated on the basis of the second illumination light image to which the sensor gain is applied is used to calculate a target light amount of the second illumination light, and thus the brightness of the second illumination light image can be matched with the second target brightness even in a case where the sensor gain varies. Since the second digital gain applied to the second illumination light image is changed according to the sensor gain, it is possible to adjust the second illumination light image to the second target brightness.

In the processor device 14, programs related to various processes are stored in a program memory (not shown). The central control unit 43 (refer to FIG. 2) configured with a processor executes the programs in the program memory to realize the functions of the image acquisition unit 40, the first target light amount calculation unit 50, the sensor gain setting unit 51, the digital gain setting unit 52, and the second target light amount calculation unit 53.

In the multi-light emission mode, the image acquisition unit 40 acquires the first illumination light image based on the first illumination light and acquires the second illumination light image based on the second illumination light. Regarding the exposure control for the first illumination light image, the first target light amount calculation unit 50 calculates a target light amount TLM1 of the first illumination light on the basis of the first target brightness related to the first illumination light image. Specifically, first, the first target light amount calculation unit 50 calculates a first brightness of observation target included in the first illumination light image from a pixel value of the first illumination light image (for example, an average value of the pixels of the entire image). In a case where the first brightness is calculated, the target light amount TLM1 of the first illumination light is calculated such that the first brightness becomes the first target brightness. The first target brightness is preferably set in advance, and it is preferable that the setting can be appropriately changed by the user interface 16 even after the setting thereof.

The target light amount TLM1 of the first illumination light is calculated on the basis of a difference value between the first brightness and the first target brightness. For example, in a case where the first brightness is lower than the first target brightness, the target light amount TLM1 of the first illumination light is calculated such that the first brightness is increased, and in a case where the first brightness is higher the first target brightness, the target light amount TLM of the first illumination light is calculated such that the first brightness is reduced.

Figure 7:
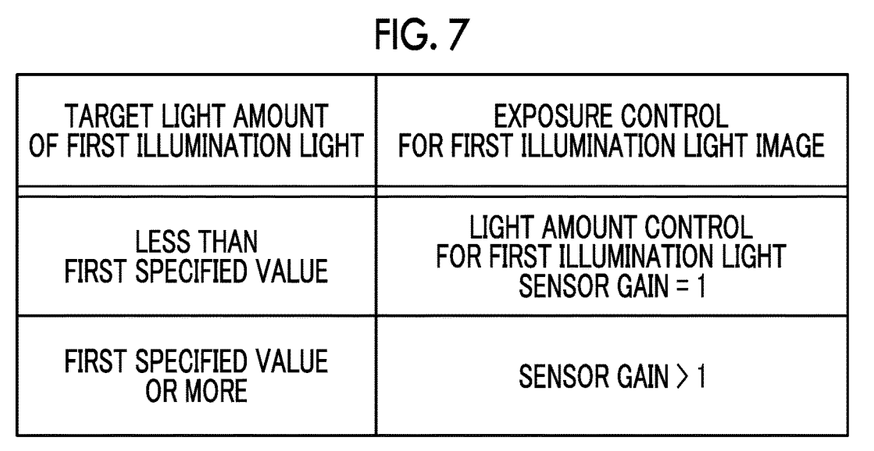
FIG. 7 is a table showing exposure control for a first illumination light image.

The exposure control for the first illumination light image differs depending on whether the target light amount TLM1 of the first illumination light calculated by the first target light amount calculation unit 50 is less than a first specified value or equal to or more than the first specified value. The first specified value is preferably the maximum amount of the first illumination light that can be emitted. As shown in FIG. 7, in a case where the target light amount TLM1 of the first illumination light is less than the first specified value, the first target brightness can be sufficiently reached by controlling a light amount LM1 of the first illumination light. Thus, the sensor gain setting unit 51 sets the fixed sensor gain to 1.

On the other hand, in a case where the target light amount TLM1 of the first illumination light is equal to or more than the first specified value, the first target brightness cannot be reached only by controlling the light amount LM of the first illumination light. Thus, the sensor gain setting unit 51 sets the sensor gain such that the sensor gain applied to the first illumination light image is more than 1. The sensor gain is preferably set according to the first target brightness. For example, it is preferable that the sensor gain is increased as the first target brightness is increased.

However, in a case where the sensor gain is increased too much, noise will be emphasized, and thus the sensor gain is set in consideration of a signal/noise ratio (S/N ratio). In a case where the sensor gain exceeds an upper limit value of the sensor gain, the sensor gain setting unit 51 preferably performs a process of clipping the sensor gain to the upper limit value of the sensor gain. The sensor gain clipping process is a process of deleting a portion where the set sensor gain exceeds the sensor gain upper limit value and thus aligning the sensor gain with the sensor gain upper limit value. The first digital gain for the first illumination light image is fixed to 1 regardless of the first target light amount TLM1.

Regarding the exposure control for the second illumination light image, the second target light amount calculation unit 53 calculates the second target brightness on the basis of the second illumination light image to which the sensor gain is applied, and calculates the target light amount TLM2 of the second illumination light on the basis of the second target brightness. Since the second target light amount calculation unit 53 calculates the second target brightness on the basis of the second illumination light image to which the sensor gain is applied, as a result, the second target brightness is calculated such that as the sensor gain is increased, the second target brightness is reduced. A method of calculating the second target brightness and a method of calculating the target light amount of the second illumination light are the same as the method of calculating the first target brightness and the method of calculating the target light amount of the first illumination light.

Figure 8:
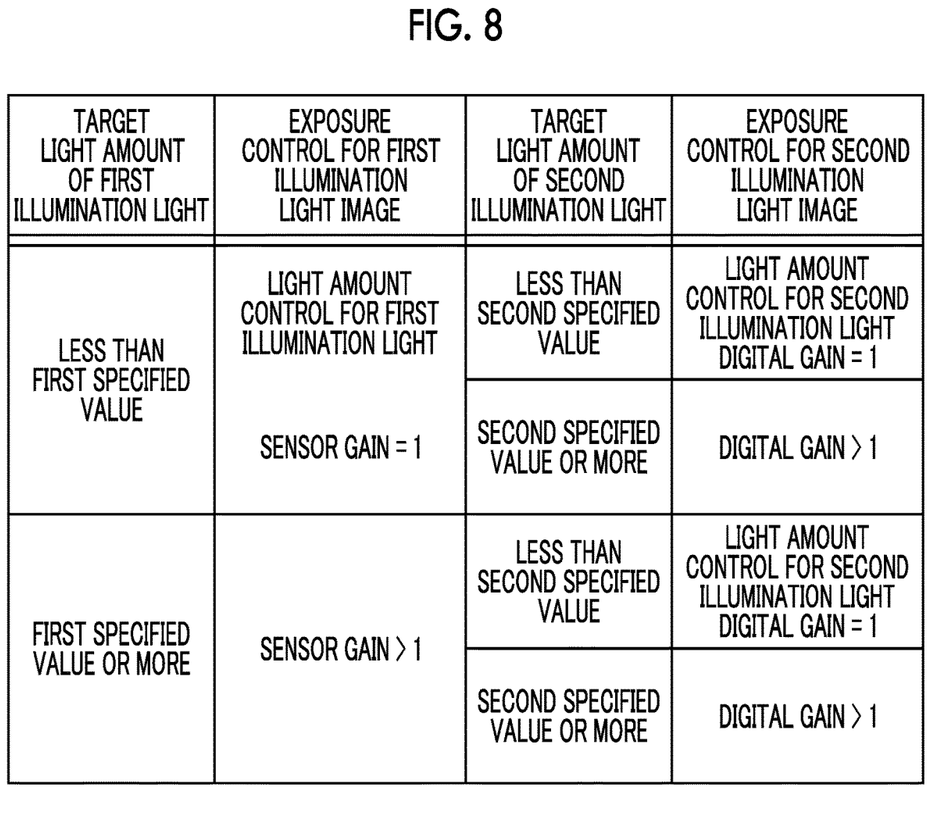
FIG. 8 is a table showing exposure control for a second illumination light image.

The exposure control for the second illumination light image differs depending on whether the target light amount TLM1 of the first illumination light calculated by the first target light amount calculation unit 50 is less than or equal to or more than the first specified value, and also differs depending on whether the target light amount TLM2 of the second illumination light is less than or equal to or more than a second specified value. The second specified value is preferably the maximum amount of the second illumination light that can be emitted.

As shown in FIG. 8, in a case where the target light amount TLM2 of the second illumination light is less than the second specified value, the second target brightness can be sufficiently reached by controlling a light amount of the second illumination light. Thus, the digital gain setting unit 52 fixedly sets the second digital gain for the second illumination light image to 1. As the sensor gain for the second illumination light image, the sensor gain determined by the first target light amount TLM1 is used as described above.

However, in a case where the target light amount TLM1 of the first illumination light is less than the first specified value, the sensor gain is fixed to 1 regardless of the light amount of the first illumination light, and thus the second brightness can be matched with the second target brightness by controlling a light amount of the second illumination light. However, in a case where the target light amount TLM1 of the first illumination light is equal to or more than the first specified value, the sensor gain is set to be greater than 1 according to the first target brightness as described above. Regarding this, in the present embodiment, in a case where the second target brightness is calculated, the second target brightness is calculated on the basis of the second illumination light image to which the sensor gain is applied, and the target light amount of the second illumination light is calculated. Therefore, even though the sensor gain varies, the second brightness can be matched with the second target brightness.

In a case where the target light amount TLM2 of the second illumination light is equal to or more than the second specified value, it is difficult to reach the second target brightness only by controlling a light amount of the second illumination light. Thus, the second digital gain is set to be greater than 1 such that the second target brightness is reached. In this case, the digital gain setting unit 52 sets the second digital gain such that the second brightness is obtained and a sum of the sensor gain and the second digital gain is less than an addition upper limit value. For example, in a case where the first target light amount TLM1 is less than the first specified value and the sensor gain is fixedly set in the sensor gain setting unit 51, the digital gain setting unit 52 sets the second digital gain according to the second target brightness within a range of the addition upper limit value.

On the other hand, in a case where the first target light amount TLM is equal to or more than the first specified value and the sensor gain is set to vary depending on the target brightness of the first illumination light in the sensor gain setting unit 51, the digital gain setting unit 52 sets the second digital gain such that as the sensor gain is increased, the second digital gain is reduced within the range of the addition upper limit value.

In a case where the sum of the sensor gain and the second digital gain exceeds the addition upper limit value, the digital gain setting unit 52 preferably performs a process of clipping the second digital gain to a digital gain upper limit value. The clipping process of the second digital gain is a process of aligning the second digital gain with a value obtained by subtracting the sensor gain from the addition upper limit value in a case where the set second digital gain and sensor gain exceed the addition upper limit value.

Figure 9:
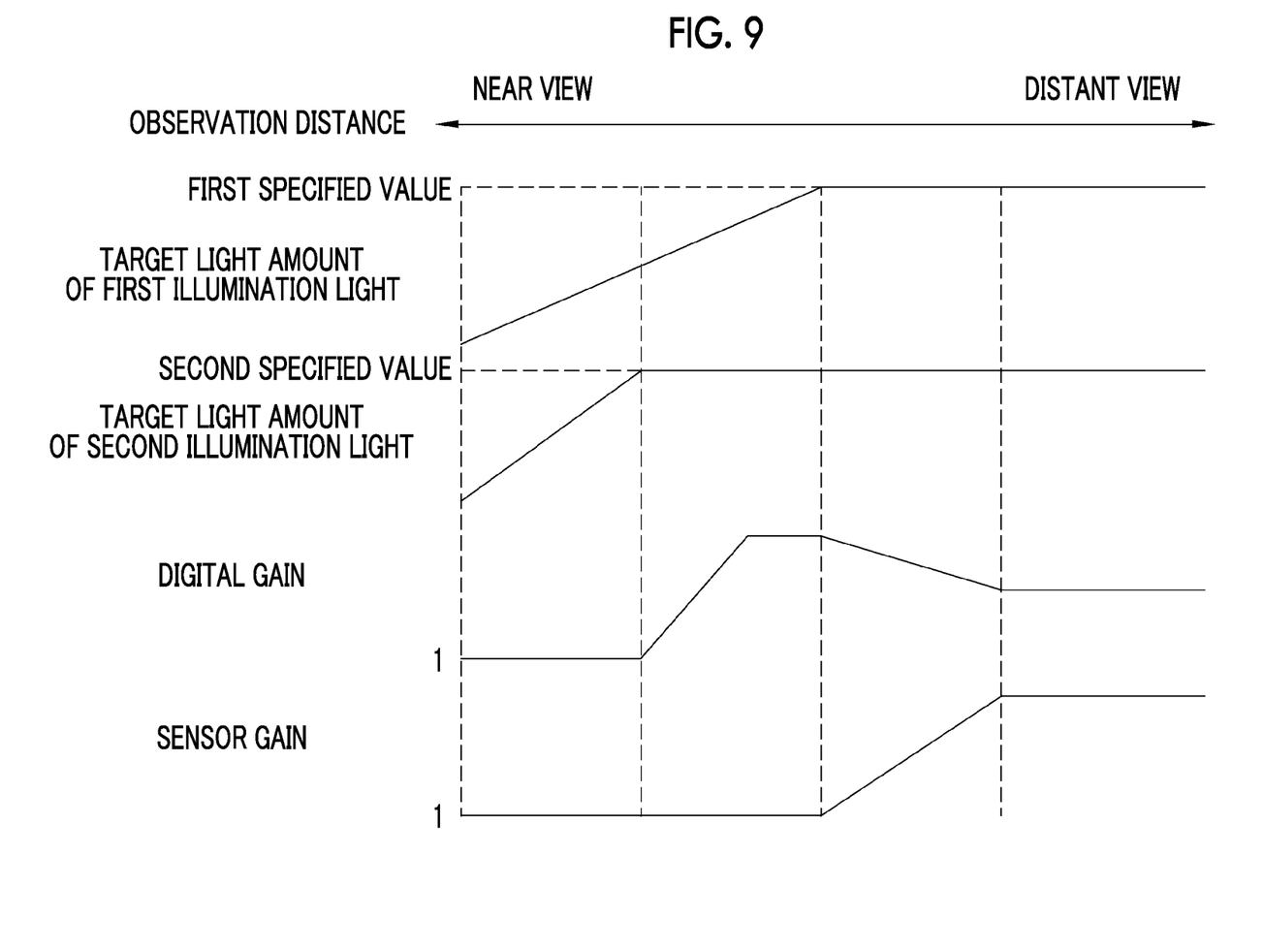
FIG. 9 is an explanatory diagram showing exposure control for a first illumination light image and a second illumination light image in a case where changing from a near view to a distant view occurs.

The exposure control for the first illumination light image and the second illumination light image performed in a case where the brightness of the observation target changes from a bright state to a dark state as in a case where changing from a near view to a distant view occurs will be described. For example, as shown in FIG. 9, in a case where the target light amount TLM2 of the second illumination light reaches the second specified value earlier than the target light amount TLM1 of the first illumination light reaches the first specified value as changing from the near view to the distant view occurs, the digital gain setting unit 52 sets the second digital gain to be greater than 1 according to the second target brightness. In this case, as the second target brightness is set to be increased in accordance with the change in brightness to the distant view, the second digital gain is set to be increased.

In a case where the target light amount TLM1 of the first illumination light reaches the first specified value, the sensor gain setting unit 51 sets the sensor gain to be greater than 1 according to the first target brightness. In this case, the sensor gain is set larger as the first target brightness increases in accordance with the change in brightness to the distant view. In this way, in a case where the sensor gain varies according to the first target brightness, the digital gain setting unit 52 prevents the sum of the sensor gain and the second digital gain from exceeding the addition upper limit value. In the exposure control in FIG. 9, the digital gain setting unit 52 reduces the second digital gain in accordance with the increase of the sensor gain.

Figure 10:
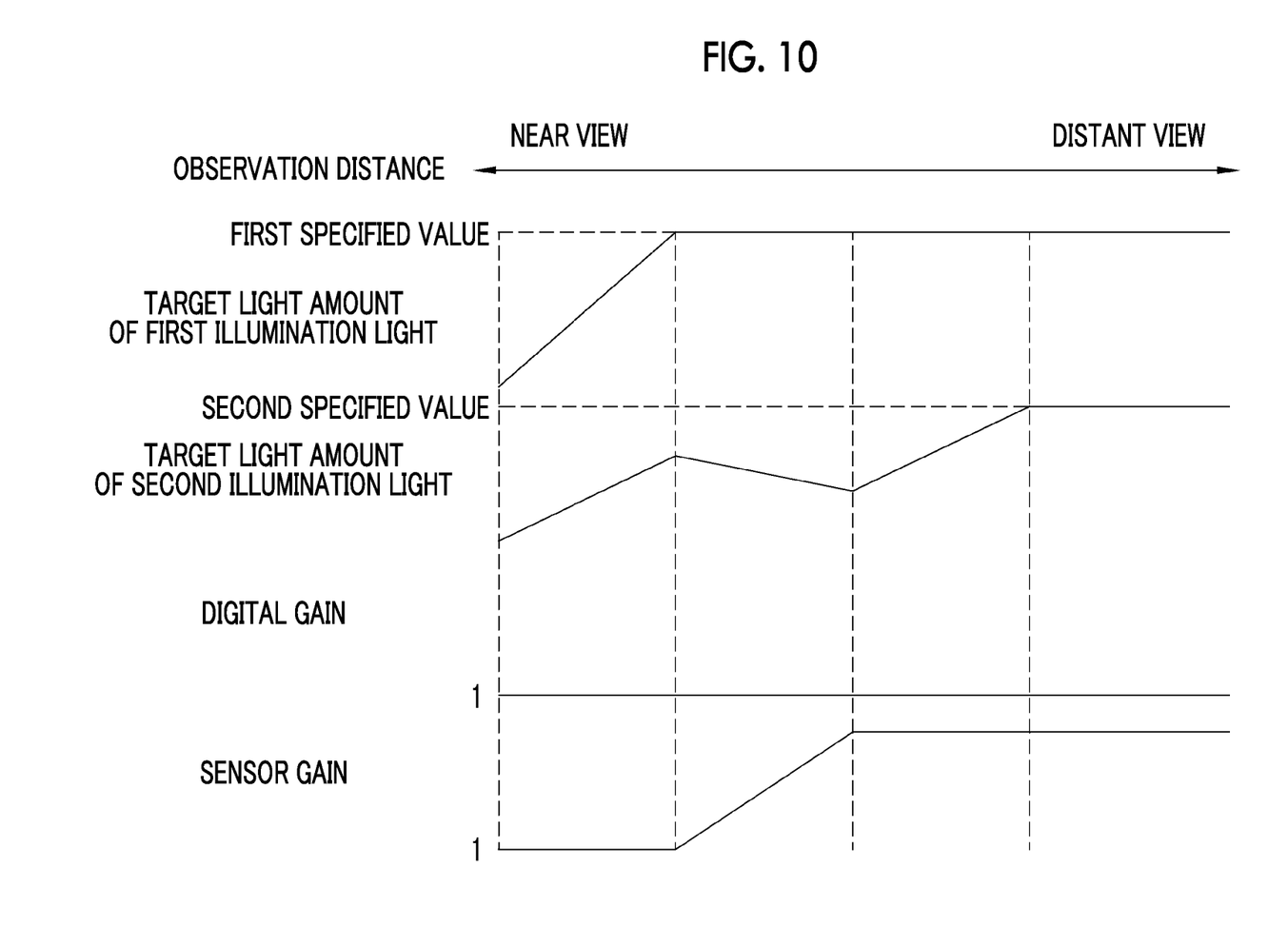
FIG. 10 is an explanatory diagram showing exposure control (different from FIG. 9) of the first illumination light image and the second illumination light image in a case where changing from a near view to a distant view occurs.

On the other hand, as shown in FIG. 10, in a case where the target light amount TLM1 of the first illumination light reaches the first specified value earlier than the target light amount TLM2 of the second illumination light reaches the second specified value as changing from the near view to the distant view occurs, the sensor gain setting unit 51 sets the sensor gain to be greater than 1 according to the first target brightness. As described above, even in a case where the sensor gain is set to be greater than 1, the target light amount TLM2 of the second illumination light is calculated on the basis of the second illumination light image to which the sensor gain is applied, and thus it is possible to match the brightness of the second illumination light image with the second target brightness.

Next, a timing at which the second digital gain is set and reflected in the second illumination light image in the multi-light emission mode will be described. Since the sensor gain is used for both the first illumination light image and the second illumination light image, the sensor gain is reflected in the first illumination light image and the second illumination light image immediately after a timing at which the sensor gain is set.

Figure 11:
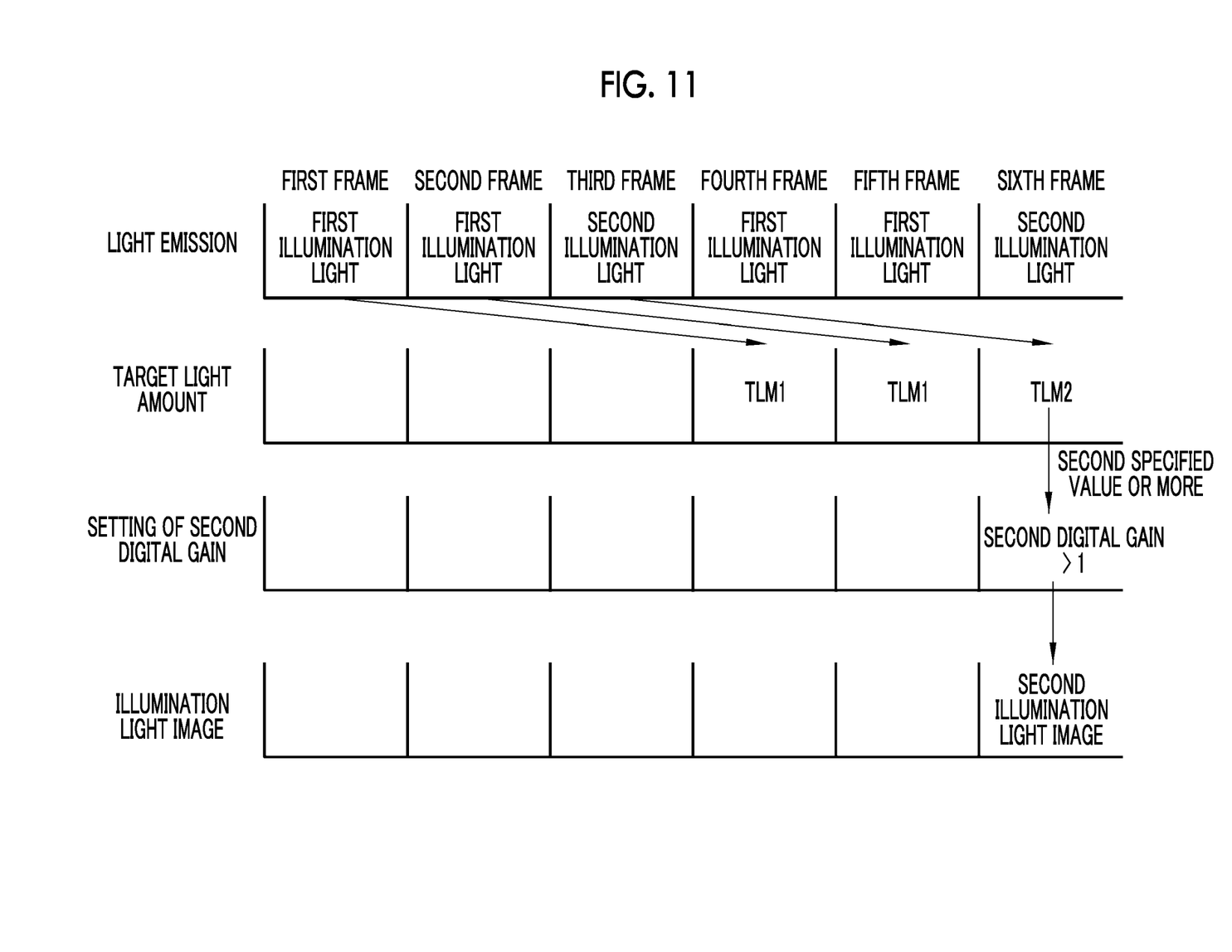
FIG. 11 is an explanatory diagram showing setting of a second digital gain.

As shown in FIG. 11, in a case where the first illumination light for two frames is continuously emitted and then the second illumination light for one frame is repeatedly emitted, the first target light amount calculation unit 50 calculates the target light amount TLM1 of the first illumination light in the fourth and fifth frames from the first illumination light image based on the first illumination light in the first and second frames. The first target light amount calculation unit 50 calculates the target light amount TLM2 of the second illumination light in the sixth frame from the second illumination light image based on the second illumination light in the third frame.

Here, in a case where the target light amount TLM2 of the second illumination light in the sixth frame is equal to or more than the second specified value, the second digital gain applied to the second illumination light image based on the second illumination light in the sixth frame is set to be greater than 1. In this case, the set second digital gain is reflected in the second illumination light image at a timing at which the second illumination light image based on the second illumination light in the sixth frame is acquired.

Figure 12:
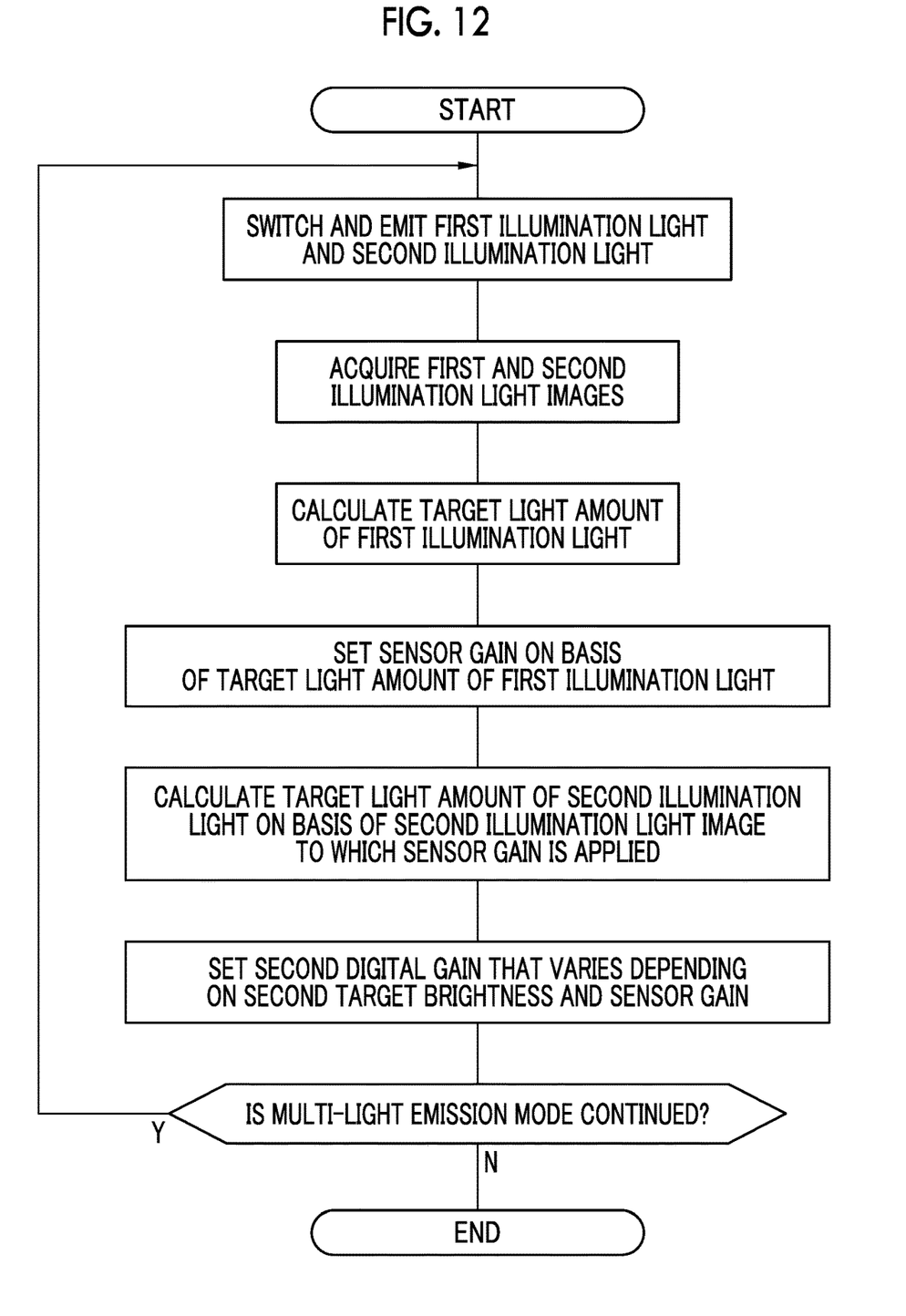
FIG. 12 is a flowchart showing exposure control in a multi-light emission mode.

Next, the exposure control for the first illumination light image and the second illumination light image in the multi-light emission mode will be described with reference to a flowchart of FIG. 12. In a case where a mode is switched to the multi-light emission mode, the first illumination light and the second illumination light having different emission spectra are automatically switched and emitted according to a specific light emission pattern. The first illumination light image is acquired by the image pick-up sensor 37 picking up an image of the observation target illuminated by the first illumination light. The second illumination light image is acquired by picking up an image of the observation target illuminated by the second illumination light.

The first target light amount calculation unit 50 calculates the target light amount of the first illumination light on the basis of the first target brightness of the first illumination light image, and calculates the target light amount of the second illumination light on the basis of the second target brightness of the second illumination light image. The sensor gain setting unit 51 sets the sensor gain applied to the first illumination light image and the second illumination light image on the basis of the target light amount of the first illumination light. The second target light amount calculation unit 53 calculates the second target brightness on the basis of the second illumination light image in which the sensor gain is reflected, and calculates the target light amount of the second illumination light on the basis of the second target brightness. The digital gain setting unit 51 sets the second digital gain, which is applied to the second illumination light image and varies depending on the second target brightness and the sensor gain. As long as the multi-light emission mode is continued, the above series of processes or the like is repeatedly performed.

In the above embodiment, hardware structures of processing units executing various processes, such as the image acquisition unit 40, the image processing unit 41, the display control unit 42, the central control unit 43, the first target light amount calculation unit 50, the sensor gain setting unit 51, the digital gain setting unit 52, and the second target light amount calculation unit 53 are various processors as described below. The various processors include a central processing unit (CPU) and/or a graphic processing unit (GPU) that is a general-purpose processor that executes a software (program) to function as various processing units, a programmable logic device (PLD) such as a field programmable gate array (FPGA) of which a circuit configuration is changed after being manufactured, a dedicated electric circuit that is a processor having a circuit configuration specially designed to execute various processes.

One processing unit may be configured with one of these various processors, or may be configured with a combination of two or more processors of the same type or different types (for example, a combination of a plurality of FPGAs, a combination of a CPU and an FPGA, or a combination of a CPU and a GPU). A plurality of processing units may be configured by one processor. As an example of configuring a plurality of processing units with one processor, first, there is a form in which one processor is configured by a combination of one or more CPUs and software, as typified by a computer used for a client or a server, and this processor functions as a plurality of processing units. Second, as typified by system on chip (SoC), there is a form in which a processor that realizes functions of the entire system including a plurality of processing units with one integrated circuit (IC) chip is used. As described above, the various processing units are configured by using one or more of the above various processors as a hardware structure.

The hardware structure of these various processors is, more specifically, an electric circuit (circuitry) in which circuit elements such as semiconductor elements are combined. A hardware structure of the storage unit is a storage device such as a hard disc drive (HDD) or a solid state drive (SSD).

EXPLANATION OF REFERENCES

10: endoscope system
12: endoscope
12a: insertion part
12b: operating part
12c: bendable part
12d: tip part
12e: angle knob
12f: observation mode selector switch
12h: still image acquisition instruction switch
12i: zoom operating part
12j: forceps port
13: light source device
14: processor device
15: display
16: user interface
20: light source unit
20a: V-LED
20b: B-LED
20c: G-LED
20d: R-LED
22: optical path coupling unit
23: light guide
30 illumination optical system
31: illumination lens
32: image pick-up optical system
35: objective lens 36: zoom lens
37: image pick-up sensor
40: image acquisition unit
41: image processing unit
42: display control unit
43: central control unit
50: first target light amount calculation unit
51: sensor gain setting unit
52: digital gain setting unit
53: second target light amount calculation unit
L1: first illumination light
L2: second illumination light
P1: first illumination light image
P2SP, P2SQ, P2SR, P2SS: second illumination light image
Pe1: first light emission period
Pe2: second light emission period

What is claimed is:

1. An endoscope system comprising:
a light source unit that automatically switches and emits first illumination light and second illumination light having different emission spectra according to a specific light emission pattern; and
a processor configured to:
acquire a first illumination light image based on the first illumination light and a second illumination light image based on the second illumination light;
calculate a target light amount of the first illumination light on the basis of a first target brightness of the first illumination light image;
sets a sensor gain applied to the first illumination light image and the second illumination light image on the basis of the target light amount of the first illumination light;
calculate a second target brightness on the basis of the second illumination light image in which the sensor gain is reflected, and calculates a target light amount of the second illumination light on the basis of the second target brightness; and
set a second digital gain that is applied to the second illumination light image and varies depending on the second target brightness and the sensor gain.

2. The endoscope system according to claim 1, wherein the processor is further configured to, in a case where the target light amount of the second illumination light is equal to or more than a second specified value, set the second digital gain such that the second target brightness is obtained and a sum of the sensor gain and the second digital gain is less than an addition upper limit value.

3. The endoscope system according to claim 2, wherein the processor is further configured to, in a case where the target light amount of the first illumination light is less than a first specified value,
set the fixed sensor gain, and
set the second digital gain according to the second target brightness within a range of the addition upper limit value.

4. The endoscope system according to claim 2, wherein the processor is further configured to, in a case where the target light amount of the first illumination light is equal to or more than a first specified value,
set the sensor gain to vary according to the target light amount of the first illumination light, and
set the second digital gain such that the second digital gain is reduced as the sensor gain is increased within a range of the addition upper limit value.

5. The endoscope system according to claim 1, wherein the processor is further configured to, in a case where the sensor gain exceeds a sensor gain upper limit value, perform a process of clipping the sensor gain to the sensor gain upper limit value.

6. The endoscope system according to claim 2, wherein the processor is further configured to, in a case where the sum of the sensor gain and the second digital gain exceeds the addition upper limit value, perform a clipping process for aligning the second digital gain with a value obtained by subtracting the sensor gain from the addition upper limit value.

7. The endoscope system according to claim 1, wherein the second target brightness is reduced as the sensor gain is increased.

8. The endoscope system according to claim 1, wherein the processor is further configured to set a fixed first digital gain that is a first digital gain applied to the first illumination light image and does not change regardless of the sensor gain, in addition to the setting of the second digital gain.

9. The endoscope system according to claim 1, wherein, in a case where the first illumination light for a plurality of frames is continuously emitted and then the second illumination light for at least one frame is emitted in the specific light emission pattern, and the second digital gain greater than 1 is set, the set second digital gain is reflected in the second illumination light image acquired after the first illumination light is continuously emitted.

10. An operation method for an endoscope system including a light source unit that automatically switches and emits first illumination light and second illumination light having different emission spectra according to a specific light emission pattern and a processor, the operation method comprising:
causing the processor to execute:
a step of acquiring a first illumination light image based on the first illumination light and a second illumination light image based on the second illumination light;
a step of calculating a target light amount of the first illumination light on the basis of a first target brightness of the first illumination light image;
a step of setting a sensor gain applied to the first illumination light image and the second illumination light image on the basis of the target light amount of the first illumination light;
a step of calculating a second target brightness on the basis of the second illumination light image in which the sensor gain is reflected, and calculates a target light amount of the second illumination light on the basis of the second target brightness; and
a step of setting a second digital gain that is applied to the second illumination light image and varies depending on the second target brightness and the sensor gain.

* * * * *